United States Patent [19]

Malyshev et al.

[11] Patent Number: 4,589,413
[45] Date of Patent: May 20, 1986

[54] SURGICAL INSTRUMENT FOR RESECTION OF HOLLOW ORGANS

[76] Inventors: Boris N. Malyshev, ulitsa Butlerova, 24, kv. 219; Viktor A. Saljuk, Teply stan, 1 Mikroraion, 7, kv. 153; Oleg X. Skobelkin, ulitsa Vesnina, 30, kv. 27; Evgeny I. Brekhov, ulitsa Marshala Timoshenko, 44, kv. 76; Boris A. Smirnov, ulitsa Borisa Galushkina, 17, kv. 26; Ivan A. Korolkov, ulitsa Polyarnaya, 52, korpus 2, kv. 174; Viktor P. Bashilov, ulitsa Akademika Pavlova, 27, korpus 2, kv. 87; Tatyana L. Ivanova, ulitsa Polyarnaya, 52, korpus 3, kv. 408, all of Moscow, U.S.S.R.

[21] Appl. No.: 515,979

[22] Filed: Jul. 21, 1983

[51] Int. Cl.[4] ............... A61B 17/10; A61B 17/32
[52] U.S. Cl. ..................... 128/305; 128/334 R; 128/303.1; 227/19; 227/DIG. 1
[58] Field of Search ............ 128/346, 334 R, 334 C, 128/305, 303.1; 227/DIG. 1, 19

[56] References Cited

U.S. PATENT DOCUMENTS

| | | | |
|---|---|---|---|
| 3,017,637 | 1/1962 | Sampson | 227/DIG. 1 X |
| 4,143,660 | 3/1978 | Malyshev et al. | 128/303.1 |
| 4,290,542 | 9/1981 | Fedotov et al. | 128/334 R X |
| 4,355,751 | 10/1982 | Kapitano et al. | |
| 4,397,311 | 8/1983 | Kanshin et al. | |

FOREIGN PATENT DOCUMENTS 511939  4/1976  U.S.S.R. .

Primary Examiner—Michael H. Thaler
Attorney, Agent, or Firm—Fleit, Jacobson, Cohn & Price

[57] ABSTRACT

The disclosure is made of a surgical instrument comprising a suturing device having a supporting body and a staple body with an ejector for ejecting staples therefrom for suturing, the bodies being coupled together by means of a pivot device adjacent one end, and a retainer is provided at the other end thereof for locking a relative position of the bodies. A cutting device is provided for cutting tissues. The pivot device is coupled to one of the bodies by means of a mechanism for moving the body in the plane thereof in parallel with itself with respect to the pivot device. The retainer is of a length which is adjustable in accordance with the amount of movement of one of the bodies.

6 Claims, 9 Drawing Figures

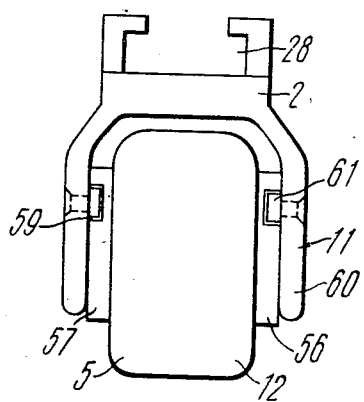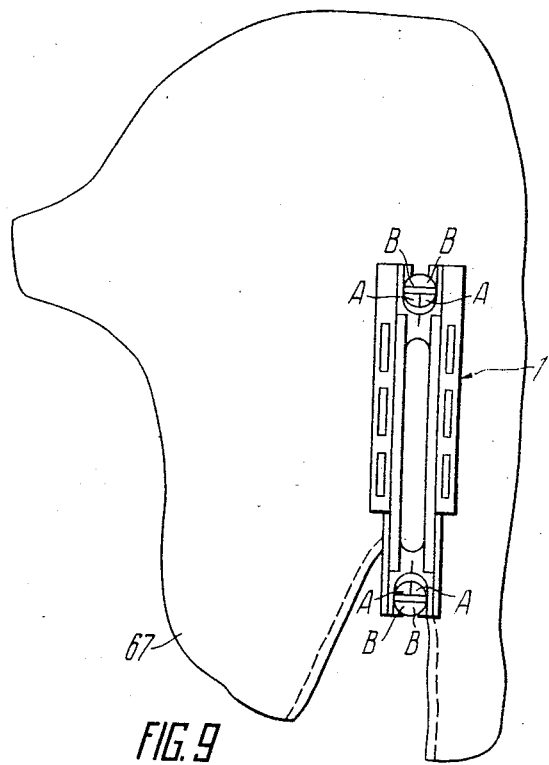

SURGICAL INSTRUMENT FOR RESECTION OF HOLLOW ORGANS

The invention relates to the medical equipment, and in particular to a surgical instrument for resection of hollow organs, e.g. for resection of stomach in cutting out a tube from the greater curvature of the stomach in esophagoplasty.

Known in the art is an instrument for resection of hollow organs, comprising a suturing device including a supporting body having depressions for bending staples, a staple body having a staple magazine, and an ejector for ejecting staples arranged on carriers, a pivot device for coupling together the staple body and the supporting body located adjacent one end of the suturing device, a retainer for locking a relative position of the bodies located adjacent the other end of the suturing device, and a cutting device (cf. U.S. Pat. No. 4,143,660 issued on Mar. 13, 1979, which apparatus can incorporate a laser head).

The pivot device comprises a rugged yoke embracing both bodies. The yoke has two pivots on which may rotate one of the bodies in the plane extending at right angles to the plane of the suturing device. The yoke supports a fork member having on its back a screw for adjusting a suturing clearance adjacent to the pivot device, a bar for measuring the suturing clearance, and lines for reading the clearance along the edge of the bar, the bar being set against one of the lines in adjusting the suturing clearance. The distance between the lines is at least 1 mm which provides only for a rough setting of the suturing clearance with an accuracy of 1 mm.

The retainer for locking a relative position of the bodies comprises a yoke having its ends pivotally fixed at the end of the body opposite to the pivot device, and a screw installed in the back.

A bar for measuring the suturing clearance adjacent to the retainer is installed on the supporting body, and lines for reading the suturing clearance at the edge of the bar are applied to the staple body, the bar being installed against one of the lines in setting the suturing clearance. The distance between the lines is also at least 1 mm so that only a rough adjustment of the suturing clearance with the accuracy of 1 mm is possible.

A groove extends along the staple body, and a toothed rack extends laterally of the groove and supports an ejector for ejecting staples installed on carriers, the ejector consisting of an individual body, gears with a drive handwheel cooperating with the toothed rack, and a wedge-shaped ejector having a removable blade.

The instrument has a mechanical cutting device in the form of a removable blade installed on the wedge-shaped ejector.

The instrument functions in the following manner: an organ being resected is placed between the staple body and the supporting body which are tied together by means of the yoke of the pivot device. The yoke fork member is turned until its back is under the yoke. Then the yoke and the bodies of the instrument are pressed together by the screw to set-up the suturing clearance as determined from the lines applied to the yoke and to the edge of the bar for measuring the suturing clearance. Then the yoke of the retainer for locking a relative position of the staple body and the supporting body of the instrument is turned with respect to the supporting body until its back is over the staple body, whereafter the staple body is pressed by the screw installed in the back of the yoke against the supporting body to set-up the suturing clearance as determined from the line applied to the staple body and to the edge of the bar for measuring the suturing clearance (the suturing clearance is the distance between the staple body and the supporting body at which the staple suture is formed).

By turning the gears by rotating the handwheel, the ejector is caused to move along the staple body. The wedge of the ejector lowers the carriers which eject the staples from the staple grooves. The staples pierce the tissue being resected with their pointed legs and abut against the depressions of the supporting body to bend into a B-shaped configuration, so as to join the tissue securely. When the ejector moves along the staple body, the blade secured to the ejector dissects the tissue.

It is not possible to set accurately the suturing clearance in this prior art instrument. The suturing clearance is non-uniform, the tissues may be crushed or undercompressed which may result in the loss of tightness and poor hemostasis in the suture and also in postoperation incompetence of the suture both with crushing and undercompression. In addition, as the suturing clearance between the staple body and the supporting body is non-uniform, the blade of the mechanical cutting device which is adjusted for an optimum tissue thickness cannot dissect the tissue in the zone of the pivot or retainer, that is in places where the tissue is of a considerable thickness, with a greater suturing clearance.

Still another disadvantage of the prior art instrument resides in an inadequate mobility of the instrument in the operation wound due to its large size (unacceptably large size is determined by the construction of the pivot, cutting and retaining devices).

In the prior art instrument the cutting device and the ejector for ejecting staples cannot be accommodated within the staple body so as to reduce the size of the instrument.

In addition, the construction of the retainer of the prior art instrument for locking a relative position of the staple and supporting bodies of the instrument does not provide for consecutive application of the instrument to the hollow organ during resection. Therefore, the instrument can only once be applied to the hollow organ in making a suture, and the length of the instrument is constant for all organs and depends on structural capabilities of a given instrument. This materially restricts the capabilities of the instrument in case a suture of a considerable length is to be made, so that the surgeon is to change over for manual suturing. In addition to the above-mentioned disadvantages, the prior art instrument is complicated in structure and difficult to use.

Moreover, it should be noted that separate determination of the clearance in various zones is complicated and inaccurate under the operation wound conditions. This generally results in human errors, non-uniform setting of the suturing clearance (the suturing clearance in the zones of the pivot device and retainer is different), and in crushing the tissue.

It is an object of the invention to provide a surgical instrument for resection of hollow organs, having a suturing device, an ejector for ejecting staples installed in carriers, a pivot device, a retainer, and a cutting device, which is so constructed as to ensure a substantial parallelism of the staple body and supporting body, accurate setting of the suturing clearance, reduction of the instrument size and lowering of suturing force.

One of important objects is to provide an instrument for resection of hollow organs of the above-described type which enables uniform application of force along the entire length of suture.

Another object of the invention is to provide an instrument for resection of hollow organs of the above-described type which ensures elimination of postoperation incompetence of sutures.

Still another object of the invention is to provide an instrument of the above-described type which eliminates crushing of the tissue during suturing owing to uniform compression of tissues along the entire length of the suture.

Among other objects is the provision of an instrument for resection of hollow organs which ensures tightness and hemostasis in the suture.

Still another object is to provide an apparatus for resection of hollow organs which ensure making a suture of practically unlimited length.

Another important object of the invention is to provide an apparatus for resection of hollow organs which is mobile within the operation wound during suturing owing to reduced size.

Among other objects is the provision of an instrument for resection of hollow organs which is simpler in construction compared to prior art instruments and which simplifies and facilitates operation of a surgeon in suturing.

These and other objects are accomplished by that in a surgical instrument for resection of hollow organs, comprising a suturing device including a supporting body having depressions for bending staples, a staple body having a staple magazine and an ejector for ejecting staples, a pivot device for coupling together the staple body and the supporting body, the pivot device being located adjacent one end of the suturing device, a retainer for locking a relative position of the bodies, the retainer being located adjacent the other end of the suturing device, and a cutting device. According to the invention the pivot device is coupled to one of the bodies by means of a mechanism for moving this body in the plane thereof in parallel with itself with respect to the pivot device, and the retainer is of a length which is adjustable in accordance with the amount of movement of one of the bodies.

The advantage of the instrument according to the invention resides in that, owing to an original construction of the pivot device, the tissue is compressed uniformly with a constant force along the entire length of the suture so as to eliminate crushing of the tissue, improve tightness and hemostasis in the suture, thereby eliminating postoperation incompetence of the suture, and to reduce the number of fatal outcomes.

Owing to an original construction of the pivot device, there is a possibility to arrange the ejector for ejecting staples inside the staple body. All this makes it possible to reduce the instrument size and to make it more mobile within the operation wound.

It should also be noted that the original construction of the pivot device and retainer makes it possible to enable a consecutive suturing during resection of a hollow organ so that a suture of unlimited length may be made by means of the instrument according to the invention.

The mechanism for movement may have different embodiments. Thus, the mechanism may be made in the form of two plates arranged on opposite sides of the staple body and installed for movement in parallel with respect to the longitudinal centerline of the body, and each plate may have a pair of inclined grooves adjacent the opposite ends, the pivot pin of the pivot device being installed in one pair of the grooves, and the retainer comprising a fork member having pins received in the other pair of the inclined grooves.

The staple body is preferably coupled to the pivot device by means of a screw pair, in which a nut is installed on the pivot pin, the threaded hole of the nut extending at right angle to the pivot pin. The retainer may be extensible and comprises a screw pair consisting of a screw and a nut.

The screw pairs preferably have screws with heads to which are applied marks, and lines are applied to the supporting body so as to set-up the marks of both pairs for a matched change in the clearance at both ends of the suturing device.

The retainer screw preferably has a pointed end.

The mechanism for moving the pivot device is designed for moving the supporting body and comprising two plates arranged on opposite sides of the staple casing and installed for movement with respect to the longitudinal centerline of the suturing device is preferably provided with a yoke for coupling together the two plates.

The plates of the mechanism for moving the pivot device preferably have marks and the opposite sides of the staple body have lines for setting-up the marks of the plates for a matched change in the clearance at both ends of the suturing device.

The mechanism for moving which is designed for moving the supporting body preferably has a groove in the supporting body for movement of a laser cutting instrument therealong, and the staple body coupled to the pivot device has a longitudinal guideway for the movement of a wedge-shaped ejector cooperating with prismatic tails of staple carriers, the mechanical cutting instrument being installed on the ejector for movement therewith.

The wedge-shaped ejector preferably comprises a screw pair consisting of a screw and a nut, the screw extending through the interior of the staple body.

The invention will now be described with reference to specific non-limiting embodiment shown in the accompanying drawings, in which:

FIG. 8 is a view of an instrument for resection of hollow organs taken along arrow A in FIG. 5;

FIG. 9 shows the application of an instrument in consecutive suturing.

All identical parts are indicated at the same reference numerals in the drawings.

Figure 1:
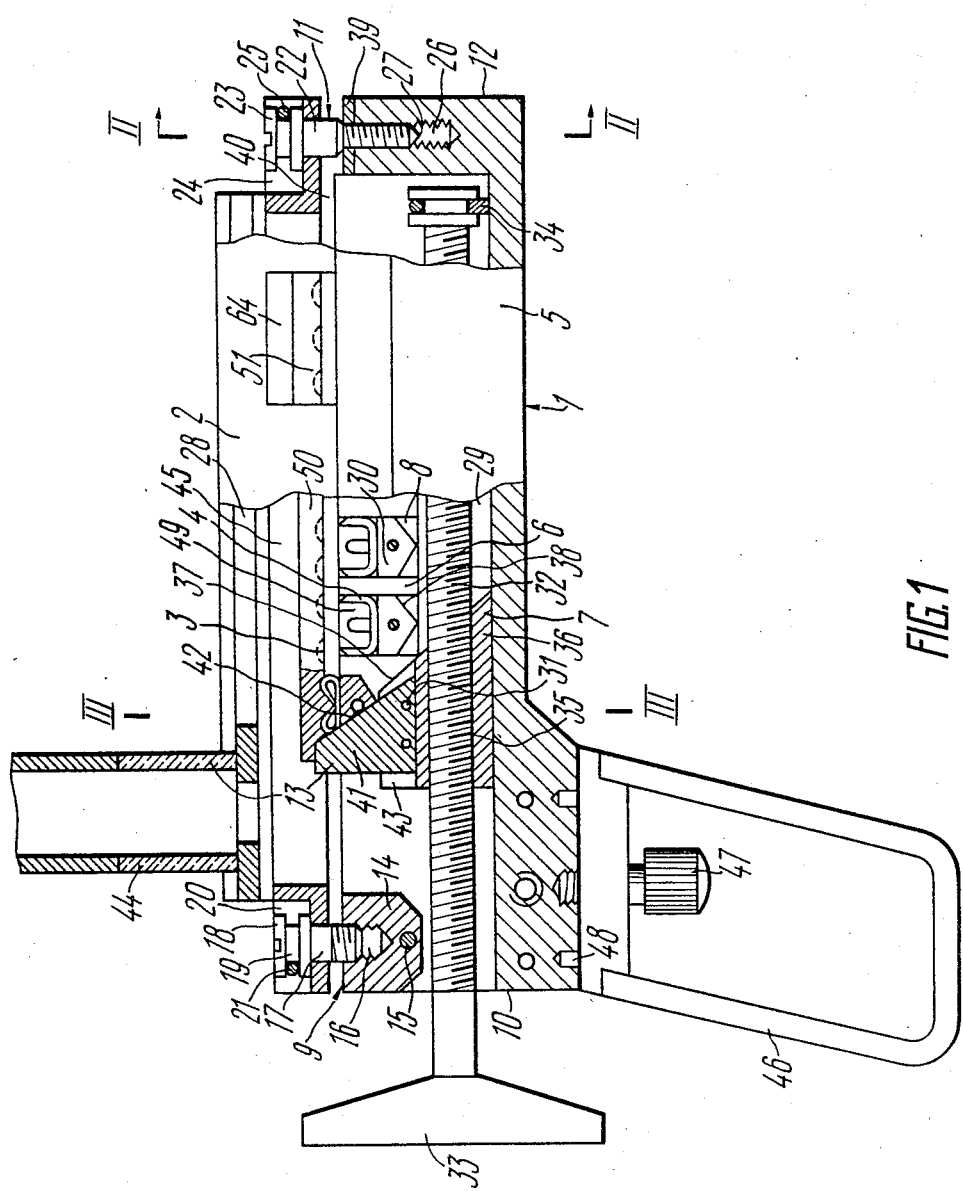
FIG. 1 shows a general view, partially in section, of an instrument for resection of hollow organs.

A surgical instrument for resection of hollow organs (FIG. 1) comprises a suturing device 1 including a supporting body 2 having depressions 3 for bending staples 4, a staple body 5 having a staple magazine 6, an ejector 7 for ejecting the staples 4 which are installed on carriers 8, a pivot device 9 for coupling the staple body 5 to the supporting body 2, the pivot device being arranged adjacent one end 10 of the suturing device 1, a retainer 11 for locking the relative position of the staple body 5 and supporting body 2, the retainer being arranged adjacent the other end 12 of the suturing device 1 and a cutting device 13. The staple body 5 which is channel-shaped is coupled to the pivot device 9 by means of a screw pair in which a nut 14 is installed on a pivot pin 15 of the pivot device 9 which is installed on the staple body 5, the threaded hole 16 of the nut extending at a right angle to the pivot pin 15. As is apparent from FIG. 1, the supporting body 2 and the staple body 5 have a closed position for a suturing operation in which, as viewed in this figure, vertical planes of the bodies both lie in a general vertical plane of the surgical instrument. The bodies 2 and 5 also are relatively movable into an open position (not shown) about the pivot pin 15 in the general vertical plane of the surgical instrument to facilitate placing of an organ to be sutured therebetween, and are relatively movable linearly with respect to the pivot pin in the general vertical plane of the surgical instrument to provide a variable suturing clearance.

The nut 14 is coupled by means of its threaded hole 16 to a screw 17 having a head 18 provided with an annular groove 19.

The screw 17 is movably coupled by means of the head 18 and a groove 20 of the supporting body 2 to the supporting body 2 and is held against longitudinal movement by a set screw 21.

The retainer 11 for locking the relative position of the staple body 5 and supporting body 2 is extensible and comprises a screw pair consisting of a screw and a nut.

A screw 22 of the retainer 11 is movably coupled by means of a head 23 and a groove 24 of the supporting body 2 to the supporting body 2 and is held against longitudinal movement by means of a set screw 25.

The nut 26 of the retainer 11 is made in the staple body 5.

The screw 22 of the retainer 11 is made with a pointed end 27.

The mechanism for moving comprising the pivot device 9 and the retainer 11 for locking the relative position of the bodies is designed for moving the supporting body 2 which has a groove 28 for movement of a laser cutting instrument therealong.

The staple body 5 coupled to the pivot device 9 has a longitudinal guideway 29 for movement of the wedge-shaped ejector 7 cooperating with prismatic tails 30 of the carriers 8 of the staples 4, the mechanical cutting instrument (knife, blade and the like) being installed on the ejector and secured by screw 31.

The wedge-shaped ejector 7 comprises a screw pair consisting of a screw and a nut, the screw extending through the interior of the staple body 5.

The screw 32 of the ejector 7 has a handwheel 33 and is journalled in the staple body 5 by means of a bearing 34 for rotation about the longitudinal axis.

The nut 35 of the ejector 7 is made in the body of a wedge 36 and has its thread coupled to the screw 32. A taper 37 is made on the wedge body 36, and tapers 38 are provided on the prismatic tails 30, the angle of taper 38 of the prismatic tail 30 with respect to the longitudinal centerline of the suturing device 1 being at least equal to the angle of taper 37 of the taper of the wedge body 36.

Figure 2:
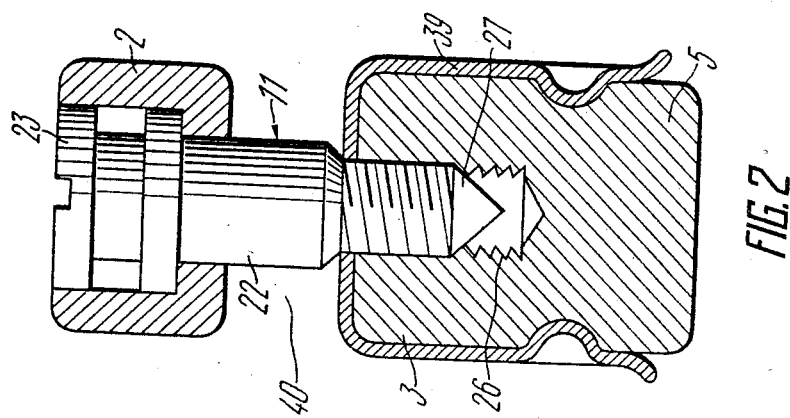
FIG. 2 is a sectional view of an instrument for resection of hollow organs taken along the line II—II in FIG. 1.

A yoke 39 is installed on the staple body 5 for equalizing a suturing clearance (the clearance 40 which is equal to the distance between the staple body 5 and supporting body 2), which is best seen in FIG. 2. A set of such yokes is supplied with each instrument in accordance with thicknesses of tissues to be sutured.

The cutting device 13 shown in FIG. 1 has two modifications. For mechanical dissection of the tissue, the cutting device 13 is used which comprises a blade 41 with a cutting edge 42 which is installed in a groove 43 of the wedge body 36.

For laser dissection of the tissue, the longitudinal through groove 28 is made in the supporting body 2, and a removable head 44 for transmitting a laser beam is installed in the groove. The removable head 44 is installed for movement along the groove 28.

For the laser beam to get to the tissue being resected so as to dissect it, a slot 45 is made through the entire thickness of the supporting body 2 in the bottom of the groove 28.

The instrument has a removable handle 46 which is secured to the staple body 5 by means of a screw 47 and pins 48.

The staple magazine 6 installed in the staple body 5 of the instrument are removable. This enables a consecutive suturing during one operation without recharging the instrument. The magazine 6 has staple grooves 49. A carrier 8 with the prismatic tail 30 and the staple 4 are installed in each groove.

Figure 3:
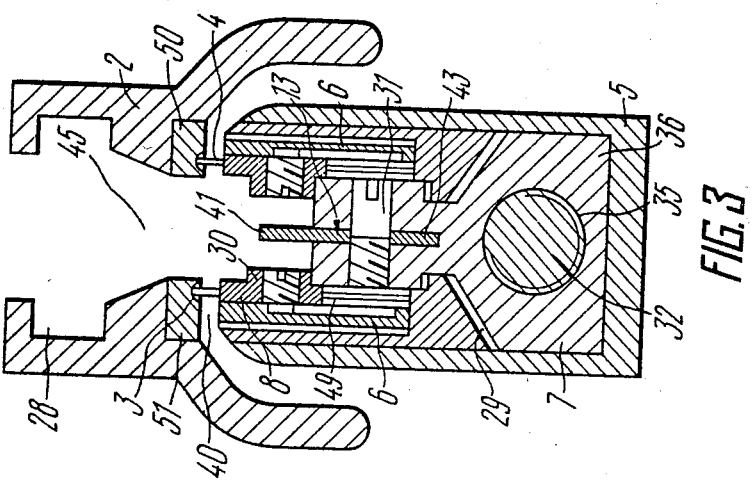
FIG. 3 is a sectional view of an instrument taken along the line III—III in FIG. 1.

Two magazines 6 are installed in the staple body 5 (FIG. 3), and two anvils 50 and 51 are installed on the supporting body 2, which have depressions 3 for bending the staples 4. The position of the depressions 3 corresponds to the position of the staple grooves 49.

Each pair of depressions 3 is positioned opposite to a respective staple groove 49.

Figure 4:
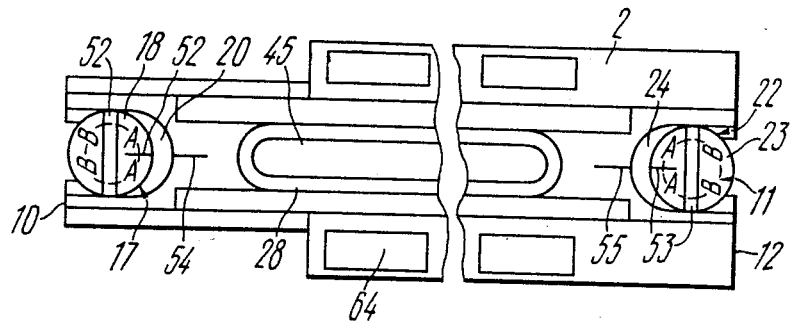
FIG. 4 is a plan view of an instrument for resection of hollow organs.

The screw pairs of the pivot device 9 (FIG. 1) and retainer 11 for locking a relative position of the staple body 5 and the supporting body 2 of the instrument have screws 17 and 22 each having heads 18 and 23, respectively. The heads (FIG. 4) have marks: marks 52 on the head 18 and marks 53 on the head 23. The marks correspond to the type of tissue to be resected.

A conventional designation of a tissue to which the mark corresponds appears adjacent each mark 52, 53. Thus, the letter "A" appears for an intestine tissue, and the letter "B" for a stomach tissue.

A line 54 is applied to the supporting body 2 for setting-up the marks 52 of the pivot screw head, and a line 55 for setting-up the marks 53 of the head of the retainer screw so as to ensure a matched change in the clearance at both ends of the suturing device.

The construction of the mechanism for moving (FIG. 1) is not limited by the above description. This construction may vary, but it should be in a strict correspondence with the object of the invention: provision of an instrument for resection of hollow organs ensuring a uniform compression of tissue (without crushing), tightness and hemostasis along the entire length of the suture. Thus, FIG. 5 shows another embodiment of the mechanism for moving.

In this embodiment the mechanism for moving the pivot device comprises two plates 56 and 57 (FIG. 6) which are arranged on opposite sides of the staple body 5 and installed for movement in parallel with respect to the longitudinal centerline of the suturing device.

Figure 5:
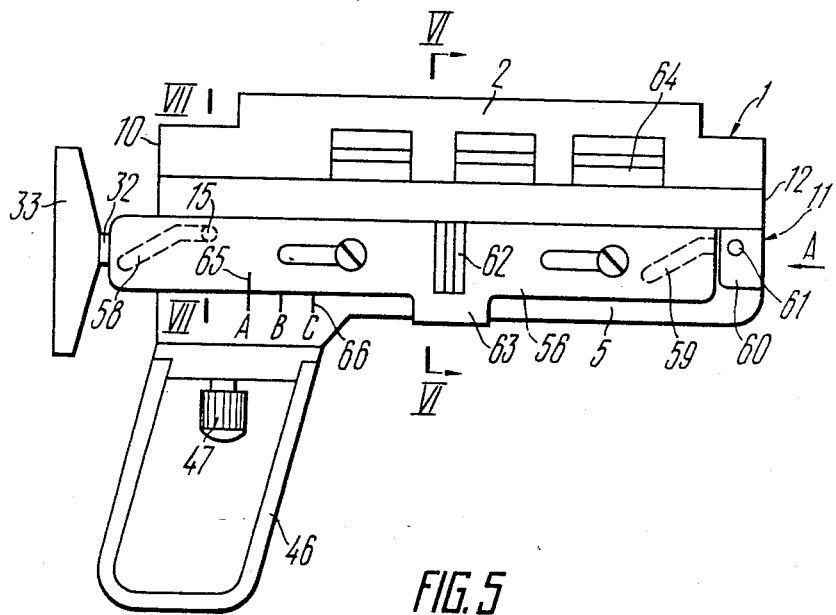
FIG. 5 is an instrument for resection of hollow organs with another embodiment of the mechanism for moving.
Figure 7:
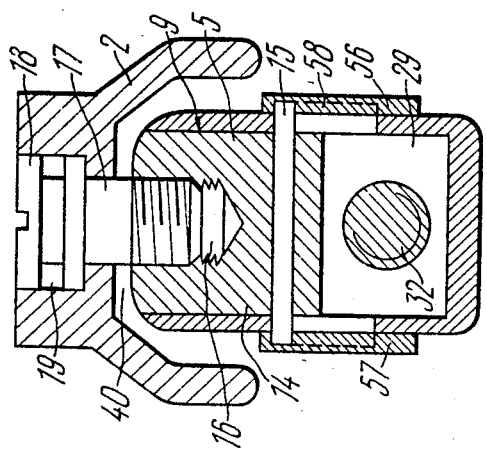
FIG. 7 is a sectional view of an instrument taken along the line VII—VII in FIG. 5.

Each of the plates (FIG. 5) has a pair of inclined grooves 58 and 59 adjacent the opposite ends, the pivot pin 15 (FIG. 7) of the pivot device being installed in one pair of grooves 58, and the retainer 11 (FIG. 8) for locking the relative position of the staple and supporting bodies comprises a fork member 60 having pins 61 which are received in the other pair of inclined grooves 59 (FIG. 5).

Figure 6:
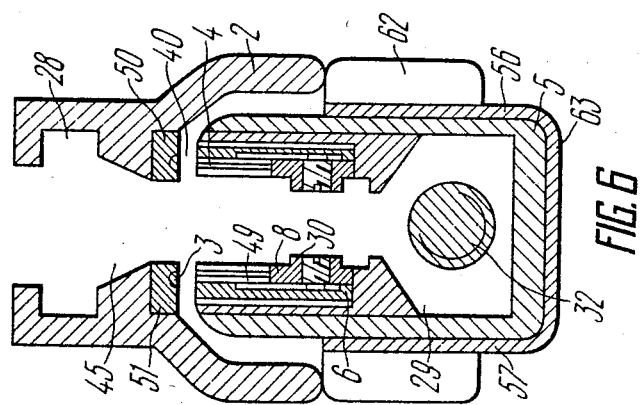
FIG. 6 is a sectional view of an instrument taken along the line VI—VI in FIG. 5.

The plates are provided with handles 62 and are coupled to one another by means of a yoke 63 for combined matched movement (FIG. 6).

To impart rigidity to the instrument without enlarging its size, the supporting body 2 (FIG. 1) is channel-shaped (FIG. 6), and its walls embrace the staple body 5 on either side.

For visual control of resection, inspection openings 64 are made in the supporting body 2 (FIGS. 1 and 5).

The instrument for resection of hollow organs according to the invention functions in the following manner.

Preparation to operation: a desired suturing clearance is adjusted between the staple body 5 and the supporting body 2. Assuming that an intestine is to be sutured, the head 18 (FIG. 4) of the pivot screw is turned in such a manner that the mark 52 with the symbol "A" should coincide with the line 54 on the supporting body 2. The yoke 39 is installed on the staple body 4 (FIGS. 1 and 2) for equalizing the suturing clearance, the yoke being coded with the letter "A" or with any other code (figure, colour, shape, design).

In case the stomach is to be sutured, the head 18 (FIG. 4) of the pivot screw is turned so that the mark 52 with the symbol "B" should coincide with the line 54 of the supporting body 2. The yoke 39 is installed on the staple body 5 (FIGS. 1 and 2) for equalizing the suturing clearance, the yoke being coded with the letter "B" or with any other code (figure, colour, shape, design). Then the operator makes it certain that the instrument is charged with staples 4 and that the wedge-shaped ejector 7 is in the initial position adjacent to the removable handle 46.

A tissue 67 (FIG. 9) to be resected is placed on the staple body and is pressed by the supporting body 2.

By turning the head 23 by means of a special screwdriver, the retainer screw is turned home, but the check should be made that the mark 53 of the head 23 of the retainer coincides with the line 55 of the supporting body. The tissue is now compressed.

In the instrument with the mechanism for moving which is made in accordance with the second embodiment (FIG. 5) the tissue is placed on the staple body 5 so as not to protrude beyond the fork member 60. Then the supporting body 2 is lowered on the tissue and locked by moving the plate 56 of the mechanism for moving towards the fork member 60 until the line 65 coincides with one of the marks 66 of the staple body 5, depending on the type of the tissue being resected. Thus, in case of the intestine tissue, the line 65 should coincide with the mark 66 with the letter "A", and in case of the stomach tissue, the line 65 should coincide with the letter "B", and the like. The tissue is now compressed.

After the tissue has been compressed, that is after an optimum clearance has been set for a given tissue, the suturing is effected (FIG. 1). In case there is no plant for generating laser radiation, or in case laser radiation is counterindicated by medical considerations, the dissection is effected by the blade 41.

The suturing is made by turning the handwheel 33 clockwise. The wedge-shaped ejector 7 moves along the staple body 5, and its taper 37 acts on the tapers 38 of the prismatic tails 30 of the carriers 8 which move along the staple groove 49 to eject the staples 4 therefrom. When the staples 4 move, they pierce the tissue being resected and abut against the depressions 3 to be bent into B-shaped configuration so as to join the tissue securely.

The blade installed in the wedge-shaped ejector moves therewith to dissect the tissue during this movement. As soon as the wedge-shaped ejector 7 reaches the end 12 of the body 5, the suturing is completed. The instrument is removed from the sutured zone of the tissue being resected.

This is done in the following manner: the screw 22 of the retainer 11 is screwed out from the nut 26 of the retainer 11 by means of a special screwdriver by rotating it counterclockwise. Then the supporting body 2 is lifted over the staple body 5 by turning it counterclockwise relative to the pivot device 9.

In the instrument having the mechanism for moving in accordance with the second embodiment (FIG. 5) the tissue is released by moving the plate 56 of the mechanism towards the handwheel 33. Then the supporting body 2 is lifted over the staple body 5 by turning it counterclockwise with respect to the pivot device 9 so as to release the tissue.

In case it is necessary by medical considerations to dissect the tissue with a laser beam, the blade 41 is removed from the wedge-shaped ejector 7, and the suturing of the resected tissue is effected without preliminary dissection of the tissue. After the suturing, when the wedge-shaped ejector 7 is at the end 12 of the staple body 5, the removable laser head 44 is installed into the groove 28 of the supporting body 2 for transmitting the laser beam, the head being displaced manually along the groove 28 to dissect the tissue between the staple grooves. With such dissection, coagulation of the fine vessels occurs, the asepsis is improved, and the tightness and hemostasis of the stamp of the hollow organ being resected are also improved. However, as noted above this is not always permitted by medical considerations, and such dissection can only be effected in case an appropriate equipment is available (clinical laser installation).

In case the necessary length of suture is greater than the length provided for by the instrument according to the invention the required length of suture may be obtained by consecutive application of the instrument (FIG. 9).

For consecutive application, only the first embodiment of the instrument can be used (FIG. 1).

With the consecutive application of the instrument the tissue being resected protrudes beyond the suture at the end 12.

In order to set the supporting body 2 and the staple body 5 relative to each other at the suturing clearance distance, the pointed end 27 of the screw 22 of the retainer 11 should pierce the tissue being resected and engage the nut 26 of the retainer 11.

After the suturing clearance is set up, the resection of the tissue is effected by one of the above-described methods.

After a length of the tissue being resected is sutured and dissected, the recharged instrument is moved along the dissection line further along the suture line, and the suturing continues. An unlimited suture length may be obtained by this method.

The instrument may be used with the employment for the dissecting of tissue of either laser radiation with all advantages derived from such radiation or mechanical cutting instrument in case such radiation cannot be recommended by medical considerations, or in case the equipment necessary for laser dissection is not available. This enlarges the field of application of the instrument compared to all prior art instruments. It makes it more flexible from the medical point of view, and more economically advantageous for clinical applications.

The construction of the pivot device and retainer ensures a desired uniform compression of tissue with a comparatively long suture with good tightness and hemostasis along the entire length of the suture so that the postoperation incompetence of sutures is reduced.

We claim:

1. A surgical instrument for resection of hollow organs, comprising a suturing device for suturing with staples including a supporting body having depressions for bending said staples, a staple body having a staple magazine for accommodating said staples, and an ejector for ejecting said staples from said magazine; a pivot device for coupling said staple body and said supporting body together for relative movement for placing an organ therebetween and for suturing it in a predetermined area, the pivot device being arranged at one end of said suturing device, a retainer for locking a relative position of the bodies arranged adjacent an opposite end of the suturing device; a cutting device; and means for moving said supporting body with respect to said staple body to vary the spacing between said bodies adjacent both ends of said suturing device and thereby ensure substantial parallelism of said bodies in a closed position; and said moving means including a mechanism for moving the pivot device, said pivot device moving mechanism being coupled to said supporting body for moving the supporting body and comprising two plates arranged on opposite sides of the staple body and installed for parallel movement with respect to the longitudinal centerline of the suturing device, each plate having a pair of inclined grooves adjacent the opposite ends thereof, with a pivot pin of the pivot device being installed in one pair of inclined grooves, and the retainer comprising a fork member having pins which are received in the other pair of inclined grooves.

2. The surgical instrument according to claim 1, wherein the staple body is coupled to the pivot device by means of a screw pair in which a nut is installed on a pivot pin, with a threaded hole of the nut extending at a right angle to the pivot pin.

3. The surgical instrument according to claim 1, wherein said mechanism for moving the pivot device and which is designed for moving the supporting body and which comprises the two plates arranged on opposite sides of the staple body and installed for movement with respect to the longitudinal centerline of the suturing device, is provided with a yoke for coupling both plates together.

4. The surgical instrument according to claim 3, wherein the plates of the mechanism for moving the pivot device have a line, and marks are applied to the opposite sides of the staple body for setting-up the plate lines for a matched change in the clearance at both ends of the suturing device.

5. The surgical instrument according to claim 1, wherein the staple body which is coupled to the pivot device has a longitudinal guideway for movement of an ejector cooperating with prismatic tails of staple carriers, the cutting device being installed on the ejector for movement therewith.

6. The surgical instrument according to claim 5, wherein the ejector comprises a pair of members in the form of a drive screw and a drive nut, the drive screw being installed for rotation in the staple body and extending through the interior of the staple body.

* * * * *